United States Patent [19]

Homma

[11] 4,120,950

[45] Oct. 17, 1978

[54] MEDICAMENT FOR PREVENTING AND TREATING PSEUDOMONAS AERUGINOSA INFECTIONS AND METHOD OF ITS PREPARATION

[75] Inventor: Yuzuru Homma, Tokyo, Japan

[73] Assignee: The Green Cross Corporation, Osaka, Japan

[21] Appl. No.: 715,198

[22] Filed: Aug. 17, 1976

[30] Foreign Application Priority Data

Feb. 5, 1976 [JP] Japan .................... 51-10866

[51] Int. Cl.$^2$ .................... A61K 39/40; C07G 7/00
[52] U.S. Cl. .................... 424/87; 260/112 B
[58] Field of Search .................... 260/112.5 R, 112 B; 424/177, 87

[56] References Cited

U.S. PATENT DOCUMENTS

| | | | |
|---|---|---|---|
| 3,838,144 | 9/1974 | Leach | 260/112.5 R |
| 3,947,575 | 3/1976 | Ondetti | 260/112.5 R |

OTHER PUBLICATIONS

Biochemica Et Biophysica Acta, 92, 1964, 351–360.
Biochimica Et Biophysica Acta, 73, 1963, 125–131.
Biochimica Et Biophysica Acta, 92, 1964, 361–366.
J. Experimental Med. 137, 1973, 183–189.
Biochimica Et Biophysica Acta, 309, 1973, 414–429.
Biochimica Et Biophysica Acta, 73, 1963, 113–124.
J. Biological Chem., 240, 1965, 3295–3302.
Chem. Org. Naturst, 23, 1967, 115–146.
R. C. Millican, et al.; J. Fectious Disease, 107, pp. 389–394.

*Primary Examiner*—Sam Rosen
*Attorney, Agent, or Firm*—Cushman, Darby & Cushman

[57] ABSTRACT

Corneal ulcer, intraperitoneal infectious diseases and serious septicemia diseases caused by infection with *P. aeruginosa* can be prevented and treated by injection of a γ-globulin aqueous solution containing a large quantity of original endotoxin protein (OEP) antibody, elastase antibody and protease antibody produced against *P. aeruginosa*.

7 Claims, 1 Drawing Figure

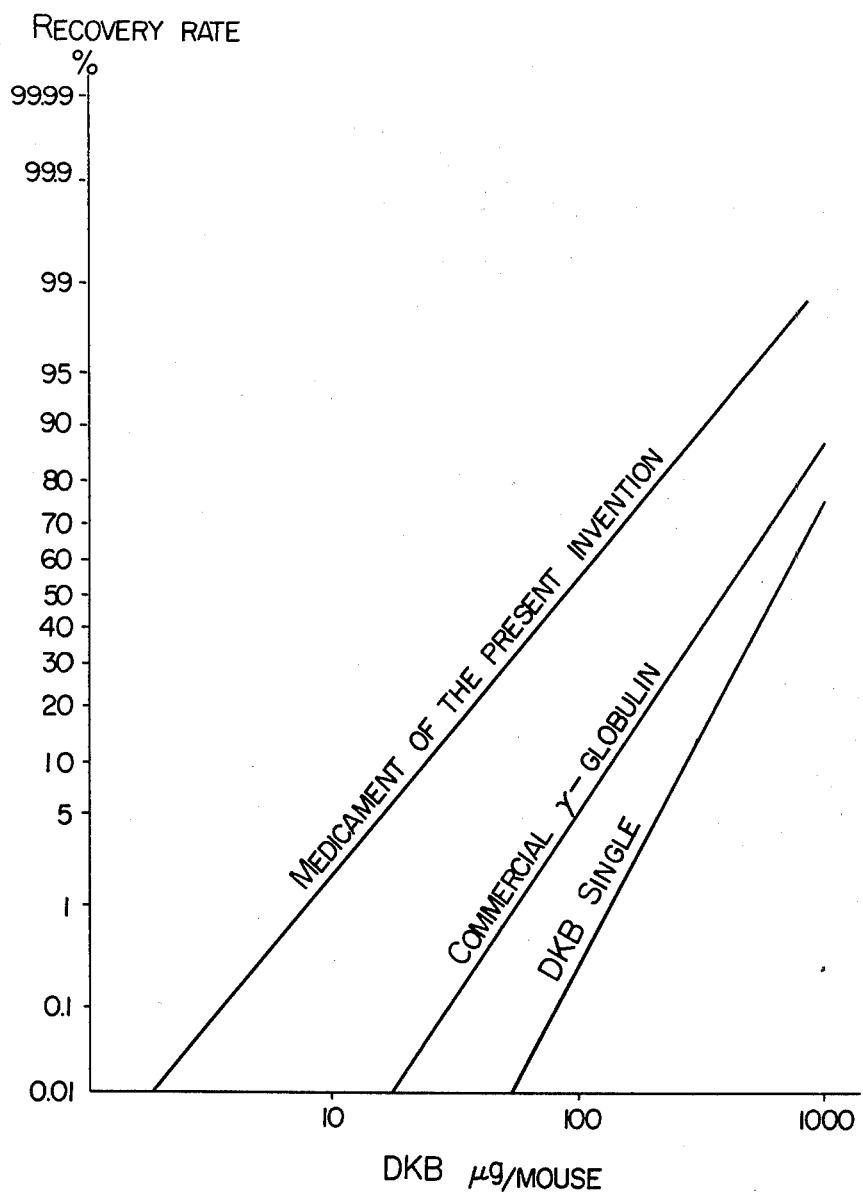

MEDICAMENT FOR PREVENTING AND TREATING PSEUDOMONAS AERUGINOSA INFECTIONS AND METHOD OF ITS PREPARATION

The present invention relates to a human γ-globulin preparation used for prevention and treatment of diseases caused by infection with *P. aeruginosa* as well as to a process of producing the gamma globulin preparation.

*P. aeruginosa* has brought forward various problems in the medical field as a representative pathogen of opportunistic infections which have become a focus of more attention with the marked progress of medical treatment today.

Infectious diseases with this bacillus often occur and are serious in the case of physiological immunoinsufficiency observed in new born babies, reduced immunofunction observed in patients who suffer from cancer, leukemia, transplantation and scald, etc. as well as when the immunofunction is inhibited by medication therapy with steroid, Immuran, etc.

A few antibiotics against *P. aeruginosa* have been developed recently, but they show hardly any efficacy in the case of insufficiency or decline of the immunofunction of the body.

Therefore improvements in the use of chemotherapy, immunotherapy or simultaneous use of both therapies has been strongly desired.

As immunotherapy, OEP (original Endotoxin Protein), a common antigen which is contained in every *P. aeruginosa* and prevents all the infectious diseases caused by this bacillus irrespective of the kind of serotypes of *P. aeruginosa* (13 kinds or more have been found today) has been isolated and named by the present inventors and already is being applied (for example, Japanese Patent Application Kokai (Laid-Open) No. 4092/73 and Jap. Exp. Med. 42, 23–34, 1972 and USP-3928565).

On the other hand the extra-cellularly produced enzymes, elastase and protease, are not always produced by every strain of *P. aeruginosa*, and the amount produced is not constant even if produced. It has generally been known that strains which produce these metabolic substances more noticeably cause more serious pathological involvement, for example, corneal ulcer, hemorrhagic pneumonea, hemorrhage from the upper part of the small intestine, septicemia, etc. In fact, other than OEP antibody, antibodies of these enzymes have been found in serum of animals having diseases caused by infection with bacteria producing these enzymes. As to the former enzyme, elastase, the process of producing the same and properties thereof are reported by the inventors in Japanese Patent Publication No. 27315/65, and J. Biol. Chem. 240, 3295–3304 (1965).

The process for producing the latter enzyme, protease, and properties thereof have been described by the present inventors in Japanese Patent Publication No. 27315/65 and Biochem. Biophys. Acta, 73, 113–124, 125–131 (1963); 92, 351–360, 361–366 (1964); 309, 414–429 (1973).

The simultaneous use of chemotherapy and immunotherapy has been carried out already, but little efficacy is shown when the immunofunction of the host side falls down resulting in the insufficiency of immunofunction. In other words, the vaccine can not be effective under such conditions, and antibiotics relying only upon bacterium inhibiting action show little efficacy unless a large dose is administered, which may produce some side reactions.

On the other hand, a simultaneous use of pharmacopoeial human immunoglobulin with antibodies has been attempted for prevention and treatment of infectious diseases caused by *P. aeruginosa* (for example, Fujii et al: abstract of 4th *P. aeruginosa* Research meeting 83–87, 1970, Shibata et al. Chemotherapy, 18, 991–999, 1971). But, attention should be paid to the fact that according to the findings of the present inventors, only a trace of OEP antibody is detected and the amount of antibody for the above mentioned elastase and protease is so slight as to be undetectable in commercial human immunoglobulin.

The object of the present invention is to present human γ-globulin to be used for immunotherapy for infections with *P. aeruginosa* especially, human gamma globulin which produces elastase and protease. This object is attained by the present invention with a medicament for preventing and treating *P. aeruginosa* infections which contains the main component of γ-globulin from human serum or plasma showing HA titers such as × 128 or more for OEP antibody, × 32 or more for elastase antibody and × 64 or more for protease antibody in 15–17% aqueous solution.

Human γ-globulin of the present invention can be produced by any well known process for obtaining γ-globulin from human plasma selecting those having high contents of OEP antibody, elastase and protease antibodies. In normal human plasma, × 8 (HA titer) for OEP antibody is detected, but protease and elastase antibodies are less than the detectable critical concentration, and none of the human immunoglobulins produced from it shows HA titers observed in the 3 kinds of antibodies provided by the present invention.

Therefore, according to the present invention, the material with higher HA titers of the above-mentioned antibodies than those of ordinary plasma is prepared from plasma or serum of any healthy people who once have suffered from *P. aeruginosa* infection or plasma or serum of healthy people whose blood shows high HA titers concerning OEP, protease and elastase antibodies resulting from administration of vaccines of OEP, protease and elastase or *P. aeruginosa* by using a single kind or mixing 2 or more kinds of human plasma, if necessary, after preliminarily determining HA titers of the aforementioned 3 kinds of antibodies in the plasma. γ-Globulin is obtained by purifying this material by an ordinary process, for example, Cohn's cold ethanol fractionation method or the ammonium sulfate fractionation method.

Moreover, the method of determining HA titer of antibodies described in this specification is described in "Pseudomonas aeruginosa and its infections (1975, published by Bunkodo)" P. 355–359, and shown as titer determined by the method based on passive hemagglutination with OEP, protease and elastase as antigens respectively.

The method is as follows:

Sheep erythrocytes are treated with CO gas and incubated in 0.6% formalin for 24 hours at 37° C. Tannic acid dissolved in phosphate buffered saline, at a concentration of 1 : 100000 is added to an equal volume of 2% cell suspension, and the mixture is incubated for 15 minutes at 37° C. Then the cells are collected by centrifugation. To the tanned cells thus obtained, an equal volume of OEP–, protease– or elastase solution is added and incubated for 15 minutes at 37° C. Then, the cells are washed with the diluent two times. Thus sensitized cells are prepared. Hemagglutinin (HA) titer is measured by passing hemagglutination reaction with the cells and expressed as the reciprocoal of the maximum globulin dilution at which hemagglutination takes place after 18 hours' standing at room temperature. The details are described by Tomiyama et al. in Jap. J. Exp. Med. 43 (3) 183–189 (1973 for the OEP, in Jap. J. Exp. Med. 45 (5) 361–365 (1975) for the protease and elastase.

The immunoglobulin of the present invention is advantageously used medicinally as an aqueous solution containing 15-17% in general just like the Japanese Pharmacopoeial human immuno-γ-globulin and is permitted to contain a protein stabilizer such as amino acetic acid and preservatives such as thimerosal in the solution. Each contained antibody having higher HA titer is more effective and × 200 or more for OEP antibody, × 64 or more for protease antibody and elastase antibody are favorable. Moreover, by treating this material with pepsin or plasmin, the complement binding property of immunoglobulin is eliminated and the γ-globulin still maintaining antibody activity can be obtained for intravenous injection. The immuno-γ-globulin of the present invention shows remarkable efficacy compared with Japanese pharmacopoeial immuno-γ-globulin when administered in combination with chemotherapy, for example, 3', 4'-dideoxykanamycin B (DKB). The ratio of efficacy observed on the basis of $ED_{50}$ obviously shows a significant difference compared with single DKB and Japanese Pharmacopoeial immuno-γ-globulin.

The γ-globulin medicament of the present invention is used for serious infectious diseases such as human corneal ulcer, intraperitoneal infectious diseases, septicemia, and meningitis caused by P. aeruginosa for which simultaneous use of chemotherapy with ordinary immunotherapy is not effective.

As the daily dose, 150 mg (1.0 ml)/kg intramusclar injection is required but the condition of patients should be taken into consideration to determine dosage and frequency for administration.

Examples of the process for producing the human immuno-γ-globulin of the present invention and that of the experiment are shown to indicate the efficacy of the treatment, but the present invention is not limited by these examples.

The attached drawing is a graph illustrating the results of the example for the experiment which shows recovery rate on the ordinate (logarithmic scale), and the simultaneously administered amount (μg/mouse) of DKB on the abscissa (logarithmic scale).

EXAMPLE

Ammonium sulfate was added to 50 ml of prepared healthy human plasma having × 32 (HA titer) of OEP antibody, × 8 (HA titer) of protease antibody and × 8 (HA titer) of elastase antibody so as to obtain 22% saturation and the resulting precipitate was isolated from the supernatant to which ammonium sulfate was further added until 33% of saturation was obtained. This precipitate was dissolved in an adequate amount of water, and the above mentioned fractionation with ammonium sulfate was repeated with this solution. γ-globulin, 200 g as dry weight, was obtained as a final precipitate which was dried and dissolved in water to prepare a 150 mg/ml solution and this aqueous solution was divided to 1 ml each, HA titers of which were × 200 for OEP antibody, × 64 for protease antibody and × 64 for elastase antibody.

EXAMPLE OF THE EXPERIMENT

The ratio of efficacies on mouse corneal infectious disease caused by living bacteria was determined with Japanese pharmacopoeial human immunoglobulin (γ-globulin content is 150 mg/ml, OEP antibody-HA titer is × 8 or less, protease antibody-HA titer and elastase antibody-HA titer are less than the detectable critical concentration) and the medicament of the present invention (γ-globulin content is 156 mg/ml, OEP antibody-HA titer is × 200, protease antibody-HA titer is × 64, elastase antibody-HA titer is × 64) by simultaneous use with the anti-P. aeruginosa antibiotic, 3',4'-dideoxykanamycin B (DKB).

The determination was carried out in accordance with the method described in Japan, J. Exp. Med. Vol. 44 (1974), P. 435–442.

dd-Y female mice (5 weeks) were used as the subject animal.

Mice were divided into groups treated by subcutaneous injection with 0.1 ml of commercial human immunoglobulin, those injected with 0.1 ml of the medicament of the present invention and untreated groups, 5 groups respectively, each group consisted of 6 mice and 90 mice were employed in total.

After 18 hours, each subject was intramusclarly injected with 0.2 ml of DKB solution prepared by dissolving DKB in physiological saline water in concentrations such as 400γ, 200γ, 100γ, 50γ and 25γ per 0.2 ml, followed by anesthetizing these mice with ether. Then the cornea was injured with a needle (size ¼) for subcutaneous injection under a stereomicroscope to cause an infection by applying 0.01 ml of $10^7$/ml suspension of P. aeruginosa IFO-1210 strain which produces elastase and protease.

The degree of damage in the cornea of each mouse was observed 5 days after the infection and classified into 1–8 grades according to degrees of corneal opacity, abscess and ulcer. 1st grade designates no pathological involvement, 2nd grade designates that a very slight opacity is observed in the corneal center, 3rd grade designates that an obvious opacity is observed in the corneal center, 4th grade shows that an opacity is observed in the whole of the cornea but transparencey can be found in the anterior chamber, 5th grade designates that a higher degree of opacity is observed in the center and no transparency is found, 6th grade designates that opacity is observed in the whole area and an abscess is found in the center, 7th grade designates that obvious opacity is observed extending over the whole area and an abscess is found in the center, and 8th grade shows that an ulcer is observed all over the cornea. Accordingly, grades 1–2 can be regarded as recovered.

The results are as shown in Table-1. $ED_{50}$ and ratios of efficacy were obtained by Litchfield-Wilcoxon's method (J. Pharmacol. Exp. Therap. 96, 99–113, 1949) with these experimental results, the results are as shown in FIG. 1 and Table-2.

Table 1

| DKB γ | Grade | | | | | | | |
|---|---|---|---|---|---|---|---|---|
| | 1 | 2 | 3 | 4 | 5 | 6 | 7 | 8 |
| 400 | 5/6 | | | | 1/6 | | | |

Table 1-continued

| DKB $_\delta$ | Grade 1 | 2 | 3 | 4 | 5 | 6 | 7 | 8 |
|---|---|---|---|---|---|---|---|---|
| Groups injected with the medicament of the present invention | | | | | | | | |
| 200 | 3/6 | 1/6 | 1/6 | | | | | 1/6 |
| 100 | 2/6 | 1/6 | 1/6 | | | | | 1/6 |
| 50 | 1/6 | 2/6 | 1/6 | | | | | 2/6 |
| 25 | | | | | 1/6 | 1/6 | | 4/6 |
| Groups injected with commercial human immunized globulin | | | | | | | | |
| 400 | 3/6 | | | 1/6 | | | | 2/6 |
| 200 | 1/6 | | 1/6 | | 1/6 | | 1/6 | 2/6 |
| 100 | | | | | | | | 6/6 |
| 50 | | | | | | | | 6/6 |
| 25 | | | | | | | | 6/6 |
| Groups untreated (administered with DKB single) | | | | | | | | |
| 400 | 1/6 | 1/6 | 2/6 | | | | | 2/6 |
| 200 | 1/6 | | | | | | 1/6 | 4/6 |
| 100 | | | | | | | | 6/6 |
| 50 | | | | | | | | 6/6 |
| 25 | | | | | | | | 6/6 |

Table 2

| | $ED_{50}$ and ratio of efficacy | | |
|---|---|---|---|
| | | Ratio of efficacy | |
| | $ED_{50}$ | DKB single | Commercial human immunized globulin |
| Medicament of the present invention | 90 γ | 3.00 | 1.80 |
| Commercial human immunized globulin | 400 γ | 0.73 | — |
| DKB single | 620 γ | — | 0.73 |

(Ratio showing any significant difference is 1.00 or more)

What is claimed is:

1. A composition suitable for preventing and eliminating infectious diseases caused by P. aeruginosa which produce elastase and protease, and which comprises a γ-globulin aqueous solution prepared from human serum or plasma showing an HA liter of at least ×128 for OEP antibodies, at least ×32 for elastase antibodies and at least ×64 for protease antibodies.

2. The composition of claim 1 containing a protein stabilizer and a preservative.

3. The composition of claim 1 free from the complement binding property of immunoglobulin and in a form suitable for intravenous injection.

4. The composition of claim 1 in which γ-globulin aqueous solution contains 15–17% of said γ-globulin.

5. A process for preventing and eliminating human corneal ulcer, intraperitoneal infectious diseases, septicemia and meningitis caused by infection with P. aeruginosa which produce elastase and protease, which comprises intramuscularly or intravenously injecting the composition of claim 1 at a dose of 150 mg/kg body weight per day in order to prevent and eliminate said above-mentioned diseases.

6. The process of claim 5 in which an antibiotic is simultaneously injected.

7. A process for preventing or eliminating an infectious disease caused by P. aeruginosa which disease is human corneal ulcer, intraperitoneal infectious disease, septicemia or meningitis, said process comprising injecting intramuscularly or intravenously a dose of the composition of claim 1 sufficient to prevent or eliminate said infectious disease.

* * * * *